(12) United States Patent
Suyama et al.

(10) Patent No.: US 6,320,086 B1
(45) Date of Patent: *Nov. 20, 2001

(54) METHOD FOR PRODUCING TRIMETHYLHYDROQUINONE

(75) Inventors: Kazuharu Suyama, Nerima-ku; Noboru Kiyota, Yokohama; Tomohiro Konishi, Kawasaki; Yasuo Matsumura, Yokohama, all of (JP)

(73) Assignee: Nippon Petrochemicals Company Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/573,624

(22) Filed: May 17, 2000

Related U.S. Application Data

(63) Continuation of application No. 09/123,318, filed on Jul. 28, 1998, now Pat. No. 6,211,418.

(30) Foreign Application Priority Data

Aug. 1, 1997 (JP) .................................................. 9-221044
Mar. 10, 1998 (JP) .................................................. 10-76712

(51) Int. Cl.[7] .................................................. C07C 37/00
(52) U.S. Cl. .......................................... 568/771; 568/763
(58) Field of Search ...................................... 568/771, 763

(56) References Cited

U.S. PATENT DOCUMENTS

| | | |
|---|---|---|
| T900,015 | 7/1972 | Thweatt . |
| 3,842,130 | 10/1974 | Kawaguchi . |
| 4,005,145 * | 1/1977 | Widmer . |
| 4,092,361 | 5/1978 | Costantini et al. . |
| 4,247,720 | 1/1981 | Baudouin . |
| 5,908,956 * | 6/1999 | Takahashi et al. . |

FOREIGN PATENT DOCUMENTS

| | | |
|---|---|---|
| 2149159 | 10/1971 | (DE) . |
| 26 57 386 | 6/1977 | (DE) . |
| 808815 | 4/1997 | (EP) . |
| 62-108835 | 5/1987 | (JP) . |
| 5-68456 | 9/1993 | (JP) . |

OTHER PUBLICATIONS

CA:88:104778 abs FR2335486, Jul. 15, 1977.*
CA:87:184078 abs DE2657386, Jun. 1977.*
CA:115:114096 abs of Bull Korean Chem Soc by Young Ae 12(3) pp. 253–254 (1991).
CA:116:236194 abs of Shiyou Huagong by Liu 20(9) pp 597–9 (1991).
CA:89:6522 abs of Indian Journal of Chem Sect B 15B(12) p. 1149 (1977).
CA:87:184078 abs of DE2657386 (Dec. 1976).
CA:96:169390 abs of Rep Inst Ind Saci Univ Tokyo 29(8) pp. 257–286 (1981).
CA:72:101630 abs of ZA 6901832, Oct. 1969.
CA:83:62478 abs of Chem Eng Progr 70(5) pp 78–84 (1974).

* cited by examiner

Primary Examiner—Jean F. Vollano
(74) Attorney, Agent, or Firm—Hollander Law Firm, P.L.C.

(57) ABSTRACT

An inexpensive method for producing trimethylhydroquinone free from the problem of the disposal of waste catalyst, which method comprises the steps of: (1) reacting isophorone in the presence of an acid catalyst and recovering β-isophorone by distillation, (2) oxidizing the β-isophorone in the presence of amorphous carbon and a base to obtain 4-oxoisophorone, (3) reacting the 4-oxoisophorone with an acid anhydride in a liquid phase or with a carboxylic acid in a vapor phase in the presence of a solid acid catalyst to obtain trimethylhydroquinones, and (4) hydrolyzing the trimethylhydroquinones to obtaining trimethylhydroquinone.

12 Claims, No Drawings

METHOD FOR PRODUCING TRIMETHYLHYDROQUINONE

This application is a Continuation of U.S. application Ser. No. 09/123,318, now U.S. Pat. No. 6,211,418, filed on Jul. 28, 1998.

BACKGROUND OF THE INVENTION (1) Field of the Invention

This invention relates to a method for producing trimethylhydroquinone from isophorone. The trimethylhydroquinone is a useful substance as an intermediate compound for preparing vitamin E.

(2) Prior Art

The following methods are mainly known for preparing trimethylhydroquinone.

In one of them, 2,3,6-trimethylphenol is sulfonated with sulfuric acid and it is then oxidized with manganese dioxide (Japanese Laid-Open Patent Publication No. 62-108835). This method is not desirable because a large quantity of heavy metal waste is produced, which have a large influence on environment. In addition, the 2,3,6-trimethylphenol as a starting material is expensive, so that the cost for the production of trimethylhydroquinone is high.

Another method relates to chloro-oxidation of 2,4,6-trimethylphenol (Japanese Patent Publication No. 5-68456). Because quite toxic chlorine is used as an oxidizing agent in this method, the process is dangerous to be worked. In addition, when organic chlorine compounds are generated as by-products, the cost for the disposal of waste is expensive.

BRIEF SUMMARY OF THE INVENTION

It is, therefore, the object of the present invention to provide an improved method for producing trimethylhydroquinone without difficulty, which method can be worked in a low cost and which is free from the problem in the disposal of waste catalyst.

That is, the primary aspect of the present invention is a method for producing trimethylhydroquinone comprising the steps of (1) to (4):

(1) Reacting isophorone in the presence of an acid catalyst and recovering β-isophorone by distillation;

(2) oxidizing the above β-isophorone in the presence of amorphous carbon such as activated carbon and a base to obtain 4-oxoisophorone;

(3) reacting the above 4-oxoisophorone with at least one member selected from the group consisting of acid anhydrides and carboxylic acids in the presence of a solid acid catalyst to obtain at least one compound represented by the following general formula [I]:

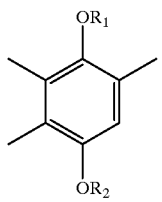

[I]

wherein each of $R_1$ and $R_2$ is a hydrogen atom or an acyl group and both of $R_1$ and $R_2$ may be the same or different; and (4) hydrolyzing the compound having an acyl group or groups in the reaction product obtained in the step (3), thereby obtaining the trimethylhydroquinone.

In the above step (3), when an acid anhydride is used, the reaction is carried out in a liquid phase. On the other hand, when a carboxylic acid is used, the reaction is carried out in a vapor phase.

A second aspect of the present invention is that the acid anhydride in the step (3) is acetic anhydride.

A third aspect of the present invention is that the solid acid catalyst used in the step (3) is an acidic ion exchange resin.

A fourth aspect of the present invention is that the product in the step (3) is at least one member selected from the group consisting of trimethylhydroquinone, 4-acetoxy-2,3,6-trimethylphenol, 4-acetoxy-2,3,5-trimethylphenol and trimethylhydroquinone diacetate.

A fifth aspect of the present invention is that the compound having an acyl group or groups are at least one member selected from the group consisting of 4-acetoxy-2,3,6-trimethylphenol, 4-acetoxy-2,3,5-trimethylphenol and trimethylhydroquinone diacetate.

According to the method of the present invention, the trimethylhydroquinone can be produced easily in a low cost without causing the problem of the disposal of waste catalyst.

DETAILED DESCRIPTION OF THE INVENTION

In the following, each preparation step will be described in more detail.

Step (1)

[Reaction of Isophorone in the Presence of an Acid Catalyst to Obtain β-isophorone by Distillation]

In this step, isophorone is reacted by adding an acid catalyst and β-isophorone having a lower boiling point is obtained by distillation. More particularly, it is possible to produce β-isophorone by reacting isophorone in the presence of an acid catalyst, and then, the β-isophorone is recovered by distillation. In another mode of reaction, the distillation is carried out while reacting isophorone in the presence of an acid catalyst, thereby recovering the β-isophorone. Because the boiling point of β-isophorone is lower than that of isophorone, they can be separated by distillation without difficulty.

In other words, the reaction to convert the isophorone to β-isophorone is an equilibrium reaction, so that when the β-isophorone is removed from the reaction system in the progress of reaction, the equilibrium is shifted to one side, as a result, the yield of β-isophorone can be raised. Accordingly, the so-called reactive distillation is preferable in this step (1), in which the distillation is performed simultaneously with the reaction of isophorone in the presence of an acid catalyst.

More particularly, when an acid catalyst in a liquid state or in a solid state, the reaction can be done such that the mixture of an acid catalyst and isophorone is put into an appropriate distillation apparatus and distillation is carried out to take out β-isophorone from the distillation apparatus. With the mode of reaction like this, the duration of distillation is the same as the duration of reaction.

When the reactive distillation is employed, any of solid acids and high boiling point liquid acids can be used as the acid catalyst. The high boiling point liquid acids are exemplified by organic acids such as adipic acid and p-toluenesulfonic acid, inorganic acids such as phosphoric acid and sulfuric acid, which have boiling points higher than those of starting materials and reaction products. The solid acids are exemplified by synthetic solid acid catalysts, natural clay solid acid catalysts, and other solid acid catalysts which are prepared by supporting inorganic acids on porous inorganic carrier substances.

Preferable solid acid catalysts are exemplified by synthetic solid acid catalysts such as silica-alumina, alumina, silica and zeolites, and natural clay minerals such as acid clay and activated clay. When zeolite is used as a solid acid catalyst, those containing hydrogen-zeolite such as HX-type zeolite, HY-type zeolite USY-type zeolite, mordenite and ZSM-5 are preferalby employed. Furthermore, it is possible to reduce the deposition of carbon to a catalyst by causing the catalyst to support an alkali metal such as sodium or potassium.

Besides the above catalysts, it is possible to use by supporting one or a combination of inorganic acids such as phosphoric acid, and heteropoly-acids of phosphotungstic acid, silicotungstic acid and silicomolybdic acid on an appropriate porous inorganic substance. More particularly, supported acid catalysts in which an inorganic acid is supported on a porous inorganic substance such as alumina, magnesia, silica and activated carbon, can be used.

Among the above-mentioned solid acid catalyst, synthetic solid acid catalysts, especially silica-alumina, HY-type zeolite, USY-type zeolite, mordenite and ZSM-5 are preferably used in view of their durability.

The duration of reaction is selected in the range of 1 minute to 200 hours in a batch-wise process.

The pressure of distillation for recovering β-isophorone is preferably lower than 1 MPa and it is not inevitable to carry out reduced pressure distillation. If appropriate, however, it is also possible to employ the reduced pressure distillation in view of the fact that low temperature operation is desirable in order to avoid the isomerization of β-isophorone. The type of distillation is not limited. When distillation is done simultaneously with the reaction, it is possible to distill together with the acid using a packed column filled with a packing such as Dickson rings. In this case, the reflux ratio is not limited, for example, it is selected in the range of 1:1 to 100:1. For the distillation, any of continuous distillation and batch-wise distillation can be employed. The composition of isophorone and β-isophorone in the distillate varies according to the conditions of reflux ratio and the kind of packing.

The β-isophorone obtained in the above step (1) is fed to the succeeding oxidation step. Because isophorone is hardly oxidized in the oxidation reaction in the step (2), it is possible to use the reactant of low purity β-isophorone which is obtained in the step (1). However, in order to facilitate the refining in the subsequent process, it is preferable to raise the purity of β-isophorone by removing isophorone. In view of this point, the purity of β-isophorone to be fed into the step (2) is in the range of 50 to 100%. When the purity of β-isophorone is low, it is possible to raise the purity by the re-distillation in an ordinary manner without catalyst. Because β-isophorone is liable to be isomerized to isophorone, the above-mentioned re-distillation is preferably done under reduced pressure.

Step (2)

[Oxidation of β-isophorone in the Presence of Amorphous Carbon Such as Activated Carbon and a Base, and Preferably Using a Gas Containing Molecular Oxygen, to Obtain 4-oxoisophorone]

In this step, β-isophorone is oxidized in the presence of amorphous carbon such as activated carbon and a base, and preferably using a gas containing molecular oxygen to obtain 4-oxoisophorone. The amorphous carbons such as activated carbons used in this step are not limited and they are exemplified by those of coconut shell origin, coal tar origin, pitch origin and charcoal origin. Furthermore, carbon black can also be used.

The specific surface area of the activated carbon is in the range of 30 to 2,000 $m^2/g$. The use quantity of the activated carbon is 0.002 to 100 parts by weight, preferably 1 to 50 parts by weight, and more preferably 5 to 30 parts by weight, per 100 parts by weight of β-isophorone. When the quantity of activated carbon is less than 0.002 parts by weight, the oxidation is hardly caused. On the other hand, when the quantity of activated carbon is more than 100 parts by weight, the handling of reactants is troublesome because the ratio of solid substance is too large in batch-wise operation.

The bases preferably used in the method of the present invention are nitrogen-containing bases, especially amines and nitrogen-containing heterocyclic bases. The amines are exemplified by triethylamine, trimethylamine, tri-n-propylamine, triisopropylamine, tri-n-butylamine, tri-n-hexylamine, trioctylamine, benzyldimethylamine, diethylamine, di-n-butylamine, and dioctylamine.

The nitrogen-containing heterocyclic bases are exemplified by pyridine, aminopyridine, chloropyridine, dichloropyridine, cyanopyridine, dimethylaminopyridine, piperidinopyridine, pyridine methanol, propylpyridine, pyrrolidinopyridine, 2,6-lutidine, 3,5-lutidine, 2,4-lutidine, 2,5-lutidine, 3,4-lutidine, 2,4,6-collidine, 1,3-di(4-piperidyl) propane, picoline, pipecoline, pyridazine, pyrimidine, dichloropyridazine, 1,8-diazabicyclo[5.4.0]-7-undecene (DBU), 1,5-diazabicyclo[4.3.0]-5-nonene (DBN), pyrazine, methylpyrazine, dimethylpyrazine, cyanopyrazine, pyrazole, dimethylpyrazole, methylpyrazolone, piperazine, methylpiperazine, dimethylpiperazine, morpholine, quinoline, isoquinoline, tetrahydroquinoline, imidazole, methylimidazole, phenylimidazole, quinaldine, triethylenediamine, piperidine, methylpiperidine, pyrrolidine, phenanthroline, and melamine.

Aliphatic amine such as triethylamine can also be used. However, the most part of triethylamine or the like is consumed by oxidation during the reaction. When the amine is oxidized, amine oxide is produced and it is further decomposed into low molecular weight aldehyde and secondary amine. The boiling point of the decomposition product of low molecular weight aldehyde is close to the boiling points of reactants and reaction solvent, so that difficulty is caused in the recovery of them by distillation. Furthermore, it is inevitable to recycle the reaction solvent in order to put the method into industrial practice economically, however, the above decomposition product is disadvantageously accumulated during the recycling operation.

Meanwhile, this problem can be solved by using an oxidation-resistant base, i.e., a difficultly oxidizable base such as a nitrogen-containing base. For this reason, an acid-resistant nitrogen-containing heterocyclic base, more preferably, pyridine is used in the method of the present invention.

In this oxidation reaction, it cannot be avoided that the methyl group on the allyl position of β-isophorone is oxidized to produce a by-product of 5,5-dimethyl-3-oxo-1-cyclohexene carbaldehyde as represented by the following structural formula [II].

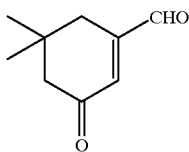

[II]

The boiling point of this compound is quite close to that of 4-oxoisophorone, so that the separation from the 4-oxoisophorone is difficult. When aliphatic amine such as triethylamine is used, the selectivity to produce the above aldehyde is as large as 12%, however, when a nitrogen-containing heterocyclic base such as pyridine is used, the selectivity is seriously reduced to a value as small as about 1%. In other words, it is quite advantageous that the isolation and refining of 4-oxoisophorone can be done economically without difficulty by using a nitrogen-containing heterocyclic base, preferably pyridine, as the base.

Therefore, in this step, it is advantageous that the contamination of reaction system due to the oxidative decomposition and the generation of undesirable by-product can be avoided by using the nitrogen-containing heterocyclic base, preferably pyridine as a base.

The use quantity of the base is 0.1 to 1,000 moles, preferably 1 to 100 moles, and more preferably 2 to 50 moles, per 100 moles of β-isophorone. When the quantity of a base is less than 0.1 mole, the oxidation hardly occurs. Even when more than 1,000 moles of a base is added, no problem is caused in the reaction, however, the effect of excess addition can not be expected any more. However, the base can be added in excess also as a solvent.

The oxidation can be attained using an optional oxidizing agent and it is done preferably using molecular oxygen. The molecular oxygen may contain an inert gas such as nitrogen. Accordingly, the oxidation in this step can be carried out by using air. For example, the oxidizing step can be done by blowing an oxygen-containing gas such as air into the reaction system.

The reaction temperature is selected in the range of 0 to 200° C., preferably 20 to 140° C., and more preferably 30 to 120° C. When the temperature is lower than 0° C., the reaction hardly proceeds, so that a very long reaction time is required. On the other hand, when the temperature is higher than 200° C., undesirable results occur in that β-isophorone is isomerized to isophorone and much polymerization product is formed to reduce the yield of 4-oxoisophorone.

The mode of reaction may be any of batch-wise and continuous. The continuous flow type reaction is desirable for industrial production. When the continuous flow type reaction is done, any type of fixed bed, moving bed and fluidized bed systems can be employed.

The duration of reaction is not especially limited. For example, in the case of batch-wise system, it is selected in the range of 1 minute to 168 hours.

The pressure of reaction is in the range of 0.1 to 10 MPa. When the pressure is lower than 0.1 MPa, the reaction rate is too low. On the other hand, the pressure above 10 MPa does not cause no trouble, however, it is not economical because a large scale pressure-resistant reactor must be used. A preferable reaction pressure is in the range of 0.5 to 6 MPa and more preferably it is in the range of 0.6 to 4 MPa. With the pressure in these ranges, the evaporation of reactants and solvent can be reduced effectively. When no pressure is applied, the loss of materials increases due to the evaporation and entrainment of contents with the blowing of the oxygen-containing gas.

After the reaction, highly pure 4-oxoisophorone is obtained from the reaction mixture by a suitable measure such as distillation, crystallization, re-crystallization, or high pressure crystallization, as occasion demands.

When the β-isophorone obtained in the step (1) using isophorone is fed as a reactant for this step, the β-isophorone sometimes contains the isophorone which was not reacted in the step (1). However, because this unreacted isophorone is hardly oxidized in the conditions of the step (2), when the reactant containing the isophorone is used, it can be recovered in this step and the recovered isophorone can be used as a feed material for the step (1).

In the next step (3), 4-oxoisophorone obtained in the step (2) is reacted with a carboxylic acid or a carboxylic acid unhydride in a vapor phase or in a liquid phase in the presence of a solid acid catalyst to obtain trimethylhydroquinone, its esters or their mixture.

More particularly, this step (3) may be any one of the following measures (3A) and (3B). That is, the step (3A) in which 4-oxoisophorone is reacted with an acid anhydride in a liquid phase and the step (3B) in which 4-oxoisophorone is reacted with a carboxylic acid in a vapor phase. In the purpose to produce trimethylhydroquinone in the method of the present invention, any of them can be employed.

In the first place, the step (3A) to react with an acid anhydride in a liquid phase will be described, and then the step (3B) to react with a carboxylic acid in a vapor phase will be described.

Step (3A)

[Both of 4-oxoisophorone and an Acid Anhydride are Brought Into Contact with a Solid Acid Catalyst in a Liquid Phase to Obtain at Least One Compound as Represented by the General Formula [I]]

The acid anhydrides are exemplified by carboxylic anhydrides such as acetic anhydride, formic anhydride, propionic anhydride, butyric anhydride, isobutyric anhydride, valeric anhydride, isovaleric anhydride, and oxalic anhydride. Among them, acetic anhydride is preferable.

The ratio of coexisting acid anhydride is more than 2 moles per 1 mole of 4-oxoisophorone, and the acid anhydride is used in excess to some extent, however, it is not necessary to use in a large excess. In the following, an example using acetic anhydride is described.

The acetic anhydride serves as a solvent as well as a reactant. Because the reaction in this step is carried out in liquid state, the reaction can be done with an appropriate solvent. When acetic anhydride which serves as a reactant as well as a solvent is employed, the liquid phase reaction can be carried out without another solvent, so that any other solvent is not always fed. However, it is of course possible to use an additional solvent. When acetic acid is used in place of the acetic anhydride, even though their chemical structures resemble each other, the selectivity for trimethylhydroquinone is very low.

It is preferable to carry out the reaction without the existence of oxygen substantially in order to avoid the oxidation of trimethylhydroquinone. Accordingly, it is possible to displace the air in the reaction system with an inert gas or to supply a small amount of inert gas into a reaction system, not only in a flow type reaction system but also in a reaction system of any other type, in order to prevent the reaction system from the invasion of oxygen. As the inert gas to be fed, nitrogen is preferable.

A solid acid catalyst is used in this step. Usable solid acid catalysts are exemplified by synthetic solid acid catalysts such as acidic ion exchange resin, silica-alumina, alumina, silica and zeolite, and natural clay minerals such as acid clay and activated clay. The acidic ion exchange resins are exemplified by strongly acidic ion exchange resin and weakly acidic ion exchange resin. When a zeolite is used as a solid acid catalyst, it is possible to use those containing hydrogen-zeolite such as HX-type zeolite, HY-type zeolite and hydrogen-faujasite. Besides them, it is possible to use one or mixture of inorganic acids such as phosphoric acid, and heteropoly-acids of phosphotungstic acid, silicotungstic acid and silicomolybdic acid supported on an appropriate porous inorganic carrier such an alumina, magnesia, silica or activated carbon.

Among the above solid acid catalysts, the acidic ion exchange resin is preferably used in view of its durability of catalytic activity. More preferable one is strongly acidic ion exchange resin catalyst. The usable strongly acidic ion exchange resin has acid groups of sulfonic acid which are connected to several resin structures such as cross-linked polystyrene skeletal structure. As a commercially available product, Amberlyst 15E (trade name, made by Japan Organo, Ltd.) can be used.

The advantage to use the solid acid catalyst in the method of the present invention depends upon the fact that the reaction process can be simplified and the recovery of acid anhydride and carboxylic acid is easy. In the following, the process of the present invention is compared with the case in which sulfuric acid is used.

When sulfuric acid is used, it is necessary to neutralize the aqueous liquid in order to remove catalyst after reaction. In this process, unreacted acid anhydride is converted into carboxylic acid by hydrolysis. Furthermore, because the carboxylic acid is soluble in water, an additional step is required to recover pure carboxylic acid.

Meanwhile, when solid acid catalyst is used, the catalyst can be separated without difficulty after reaction, so that neither the addition of water nor the neutralization is necessary. Because no water is added, the unreacted acid anhydride is not subjected to hydrolysis and the acid anhydride can be recovered as it stands. The liquid obtained by the reaction is a mixture of trimethylhydroquinones, unreacted feed materials, acid anhydride and carboxylic acid produced by the reaction, so that this reaction mixture can be refined by distillation or any other measure.

By using the solid acid catalyst as described above, the treating process can be simplified and the recovery of unreacted substances and the refining of reaction product are made easy to produce economical advantages, The reaction temperatures are determined in accordance with the kind of used catalyst, the duration of contact between reactants and catalyst, and the ratio of dilution of reactants to reaction medium. It can be selected in the range of −40 to 300° C., preferably 0 to 300° C., and more preferably 10 to 150° C. The reaction temperature above 300° C. is not desirable because side reactions increase and the coking of catalyst is intensive to reduce seriously the selectivity. The reaction temperature below −40° C. is not desirable either in economical viewpoint because the rate of intended reaction is low.

The mode of reaction may be any of batch-wise and continuous. The continuous flow type reaction is desirable for industrial production. When the continuous flow type reaction is done, any type of fixed bed, moving bed and fluidized bed systems can be employed.

The pressure of reaction is not especially limited as far as the reaction phase is maintained in liquid. The pressure may be 1 MPa or lower, preferably lower than 0.5 MPa, and more preferably lower than 0.2 MPa.

The contact time between reactants and a catalyst both in batch-wise reaction and continuous flow reaction is in the range of 1 second to 100 hours, preferably 1 minute to 50 hours. When the contact time is shorter than 1 second, the degree of conversion is low. If the contact time is longer than 100 hours, side reactions occur, for example, the produced trimethylhydroquinone is polymerized, as a result, the selectivity is lowered.

As described above, the products in the above reaction are any one of or the mixture of trimethylhydroquinone, 4-acetoxy-2,3,6-trimethylphenol, 4-acetoxy-2,3,5-trimethylphenol and trimethylhydroquinone diacetate. When the reaction product is a mixture of the above compounds, its composition varies with reaction conditions. However, any of the 4-acetoxy-2,3,6-trimethylphenol, 4-acetoxy-2,3,5 -trimethylphenol and trimethylhydroquinone diacetate other than the trimethylhydroquinone, can be converted into trimethylhydroquinone by means of ordinarily known hydrolysis.

It is possible to obtain highly pure intended product from the reaction mixture by distillation, crystallization, re-crystallization or pressurized crystallization as occasion demands.

When unreacted 4-oxoisophorone exists, it can be recovered easily by distillation and be reused. The 4-oxoisophorone does not pertain substantially to the reaction under the conditions of the next step (4), so that it is serviceable as a inert solvent. Accordingly, the reaction mixture of this step (3) can be fed to the next step (4) without removing the unreacted 4-oxoisophorone and, after the hydrolysis in the step (4), the 4-oxoisophorone may be recovered.

Step (3B)
[Both of 4-oxoisophorone and a Carboxylic Acid are Brought Into Contact with a Solid Acid Catalyst in a Vapor Phase to Obtain at Least One Compound as Represented by the General Formula [I]]

The carboxylic acid in this step serves as a reactant. In addition, when the reaction is done in a flow reaction system, it serves also as a reaction medium. The carboxylic acids used herein are exemplified by acetic acid, formic acid, propionic acid, butyric acid, isobutyric acid, valeric acid, isovaleric acid, oxalic acid, adipic acid, malonic acid and fumaric acid. Among them, acetic acid, formic acid and propionic acid are preferable, and the acetic acid is more preferable. In the following, the example using the acetic acid will be described.

Because the acetic acid is used in excess, it serves as a reaction medium as well as a reactant in a flow type reaction system as described above. In the flow type reaction system, steam is generally used as a medium. The steam is advantageous because it is inexpensive and it condenses when it is cooled to facilitate the recovery of reaction product. It is to be noted, however, that the use of steam is not appropriate because the selectivity for 4-oxoisophorone to the compound represented by the formula [I] (hereinafter referred to as "trimethylhydroquinones") is low.

As other mediums, nitrogen flow and hydrogen flow are exemplified. They are, however, expensive. In addition, they cannot be condensed by cooling them, so that reaction products are entrained in the gas flow in the form of mist, which makes the recovery of product difficult. Accordingly, this method is not suitable for the industrial mass production.

When acetic acid is used, the recovery of reaction product is easy because the acetic acid condenses when it is cooled. Further important point is that the selectivity for trimethylhydroquinones can be improved by the use of acetic acid. When acetic anhydride, a derivative of acetic acid, is used as a medium, the selectivity for trimethylhydroquinone is quite worse.

In order to avoid the oxidation of trimethylhydroquinone, a small amount of inert gas may be fed to the reaction system not only in the flow system but also in any other reaction system. The inert gas is preferably nitrogen.

When the acyl group or groups in the foregoing formula [I] are an acetyl group or groups, the reaction product in this step is at least one of trimethylhydroquinone, 4-acetoxy-2,3,6-trimethylphenol, 4-acetoxy-2,3,5-trimethylphenol and trimethylhydroquinone diacetate.

A solid acid catalyst is used in this step. Preferable solid acid catalysts are exemplified by synthetic solid acid catalysts such as silica-alumina, alumina, silica and zeolite, and natural clay minerals such as acid clay and activated clay. When a zeolite is used as a solid acid catalyst, it is possible to use those containing hydrogen-zeolite such as HX-type zeolite, HY-type zeolite and hydrogen-faujasite. It is preferable to use HY-type zeolite, USY-type zeolite, mordenite and ZSM-5. Furthermore, it is possible to reduce the deposition of carbon to catalyst by causing the catalyst to support an alkali metal such as sodium or potassium.

In addition, it is possible to use one or the mixture of inorganic acids such as phosphoric acid, and heteropoly-acids of phosphotungstic acid, silicotungstic acid and silicomolybdic acid supported on an appropriate porous inorganic carrier. Carrier-supported acid catalysts are exemplified by those in which an inorganic acid is supported on a porous inorganic substance such as alumina, magnesia, silica or activated carbon.

Among the above solid acid catalysts, the synthetic solid acid catalysts such as silica-alumina, HY-type zeolite, USY-type zeolite, mordenite and ZSM-5 are preferably used in view of their durability as catalysts. In view of the selectivity in the reaction, the silica-alumina is especially preferred.

The reaction temperatures are determined in accordance with the kind of used catalyst, the duration of contact between reactants and catalyst, and the ratio of dilution of reactants to reaction medium. It can be selected in the range of 100 to 600° C., preferably 200 to 500° C., and more preferably 250 to 400° C. The reaction temperature above 600° C. is not desirable because side reactions increase and the coking of catalyst is intensive to reduce seriously the selectivity. The reaction temperature below 100° C. is not desirable either in economical viewpoint because the rate of intended reaction is low.

During the reaction in this step, the activity of catalyst is gradually reduced by the coking with the long time use of catalyst, however, the initial catalytic activity can be recovered by decoking with air at a high temperature of, for example, 500° C.

The mode of reaction may be any of batch-wise and continuous. The continuous flow type reaction is desirable for industrial production. When the continuous flow type reaction is employed, any type of fixed bed, moving bed and fluidized bed systems can be employed.

In this step, the reaction is carried out in a vapor phase. The liquid phase reaction is not desirable because the polymerization of reactants or products markedly increases.

The pressure of reaction is not especially limited as far as the reaction is in a vapor phase. The pressure may generally be 1 MPa or lower, preferably lower than 0.5 MPa, and more preferably lower than 0.2 MPa.

The contact time between reactants and a catalyst in the continuous flow reaction is in the range of 0.001 second to 100 seconds, preferably 0.01 second to 5 seconds. When the contact time is shorter than 0.001 second, the degree of conversion is too low. If the contact time is longer than 100 seconds, the side reaction such as the polymerization of produced trimethylhydroquinones increases, as a result, the selectivity is lowered. In the batch-wise reaction, the contact time is in the range of 10 minutes to 10 hours.

The gas which is taken out from a reactor is immediately cooled into a liquid. If necessary, it is possible to recover by passing the gas through an absorbing liquid such as a hydrocarbon. A highly pure intended product can be obtained by distillation, crystallization, re-crystallization or pressurized crystallization as occasion demands.

When unreacted 4-oxoisophorone exists, it can be recovered easily by distillation and reused. The 4-oxoisophorone does not pertain substantially to the reaction under the conditions of the next step (4), so that the reaction mixture in this step can be fed to the next step (4) without removing the unreacted 4-oxoisophorone and, after the hydrolysis in the step (4), the 4-oxoisophorone may be recovered.

Step (4)
[To Obtain the Intended Trimethylhydroquinone by Hydrolyzing the Reaction Product of the Step (3A) or Step (3B)]

In the foregoing step (3A) or step (3B), the trimethylhydroquinone intended in the present invention is obtained. In many cases, however, the trimethylhydroquinone is produced in the form of its esters. Accordingly, the trimethylhydroquinone can be obtained by hydrolyzing these compounds.

An example of the compound of formula [I] in which the acyl group is acetyl group will be described. In this case, as described above, the compounds as represented by the formula [I] are 4-acetoxy-2,3,6-trimethylphenol, 4-acetoxy-2,3,5-trimethylphenol and trimethylhydroquinone diacetate.

The trimethylhydroquinone can easily be obtained by hydrolyzing these compounds having acyl groups. In this step, a catalyst is used for hydrolyzing these compounds having acyl groups. As the catalyst, any of acid catalyst and base catalyst can be used.

The solid acids of proton acids and Lewis acids are used as the acid catalysts. The proton acids are exemplified by sulfuric acid, hydrochloric acid, nitric acid, phosphoric acid, perchloric acid, and carboxylic acids such as formic acid, acetic acid and adipic acid. The sulfuric acid is especially preferable. The Lewis acids are exemplified by aluminum chloride, boron trifluoride, boron trifluoride ether complex, iron chloride and zinc chloride. The solid acid catalysts are exemplified by synthetic solid acid catalysts such as silica-alumina, alumina, silica and zeolites, and natural clay minerals such as acid clay and activated clay. When zeolite is used as a solid acid catalyst, it is possible to use those containing hydrogen-zeolite such as HX-type zeolite, HY-type zeolite or hydrogen-faujasite. Preferably, HY-type zeolite, USY-type zeolite, mordenite or ZSM-5 are used. Furthermore, it is possible to reduce the deposition of carbon to catalyst by causing the catalyst to support an alkali metal such as sodium or potassium.

Besides the above ones, it is possible to use by supporting one or a combination of inorganic acids such as phosphoric acid, heteropoly-acids of phosphotungstic acid, silicotungstic acid and silicomolybdic acid on an appropriate porous inorganic substance. More particularly, acid-supported catalysts in which an inorganic acid is supported on a porous inorganic substance such as alumina, magnesia, silica or activated carbon, can be used.

Among the above-mentioned solid acid catalysts, synthetic solid acid catalysts, especially silica-alumina, HY-type zeolite, USY-type zeolite, mordenite and ZSM-5 are preferably used.

Meanwhile, the base catalysts are exemplified by inorganic acids such as sodium hydroxide, potassium hydroxide, calcium hydroxide barium hydroxide, sodium hydrogen carbonate and potassium hydrogen carbonate, alkoxides such as sodium methoxide and sodium ethoxide, amines such as triethylamine and pyridine, and ammonia.

In order to avoid the oxidation of trimethylhydroquinone produced by the hydrolysis in this step, the reaction can be carried out without the substantial existence of oxygen. For the purpose of eliminating the existence of oxygen, the reaction is done in the environment of an inert gas such as nitrogen. When the temperature of hydrolysis is high, the effect of protection with the inert gas is large. In the industrial practice, nitrogen is desirable as an inert gas.

The mode of reaction may be any of batch-wise and continuous. The use of a solid acid as a catalyst facilitates the flow type reaction.

As the medium for flow type reaction, steam is commonly used. The steam is inexpensive and the recovering of reaction product is made easy because the steam is condensed by cooling.

In accordance with the kind of used catalyst, contact time between catalyst and reactants, and the ratio of dilution of reactants and medium, the reaction temperature is selected in the range of 0 to 600° C., preferably 50 to 300° C., and more preferably 100 to 250° C. The reaction temperature higher than 600° C. is not desirable because the side reactions increase and the coking of catalyst occurs seriously to lower the selectivity. The reaction temperature below 0° C. is not desirable in economical viewpoint because the rate of reaction is too low.

During the reaction in this step, the activity of catalyst is gradually reduced by the coking with the long time use of catalyst, however, the initial catalytic activity can be recovered by decoking with air at a high temperature of, for example, 500° C.

In a flow type reaction, as far as the reactant and reaction product are in a vapor phase, the pressure of reaction is not especially limited. The pressure of reaction is generally 1 MPa or lower, preferably lower than 0.5 MPa and more preferably lower than 0.2 MPa.

The contact time between reactants and a catalyst in continuous flow reaction in a vapor phase is in the range of 0.001 second to 100 seconds, preferably 0.01 second to 5 seconds. When the contact time is shorter than 0.001 second, the degree of conversion is too low. If the contact time is longer than 100 seconds, the side reaction such as the polymerization of produced trimethylhydroquinone increases. In the batch-wise reaction, the contact time is in the range of 10 minutes to 10 hours.

In the flow type reaction, the gas which is taken out from a reactor is immediately cooled into a liquid. If necessary, it is possible to recover by passing the gas through an absorbing liquid such as a hydrocarbon.

It is possible to obtain highly pure intended product from the reaction mixture by distillation, crystallization, re-crystallization or pressurized crystallization as occasion demands.

When the feed material to this step (4) contains 4-oxoisophorone, it can be recovered by distillation of a filtrate. The recovered 4-oxoisophorone can be used as a feed material to the step (3).

The method of the present invention comprises the combination of 4 steps and it is possible to produce trimethylhydroquinone without difficulty from inexpensive isophorone.

The present invention will be described in more detail with reference to several examples, in which the unit "%" means "percent by weight" unless otherwise indicated.

EXAMPLE 1

Step (1)

To 2 liter flask were fed 1,106 g of isophorone and 76 g of adipic acid and a distillation column (50 cm in length and filled with 3 mm Dickson rings) was attached. Distillation was carried out under ambient pressure at a reflux ratio of 60:1. When the flow rate of effluent was 7.6 g/h, β-isophorone of 95% purity (by gas chromatography) and 184° C. in boiling point was obtained. Further, when the flow rate of effluent was 12.1 g/h, β-isophorone of 93% purity and 184° C. in boiling point was obtained.

EXAMPLE 2a

Step (2)

To a 200 ml autoclave were fed 50.0 g of β-isophorone, 5.0 g of activated carbon (for chromatography use, made by Wako Pure Chemical Industries, Ltd.), 11.1 g of pyridine and 63.3 g of acetone. These contents were heated to 100° C. and air was introduced through a blowing tube with stirring. The flow rate of air was regulated to 400 ml/min (as of atmospheric pressure) and the internal pressure was regulated to 3.0 MPa. The concentration of oxygen in the waste gas was measured with an oxygen analyzer. After the reaction for 4 hours, the reaction mixture was cooled to a room temperature and excess air was released. Removing the catalyst by filtration, 124 g of filtrate was obtained. This was analyzed by gas chromatography with an internal standard of isobutylbenzene, the degree of conversion of β-isophorone was 99.8% and the selectivity for 4-oxoisophorone was 73.8%. The results are shown in the following Table 1.

EXAMPLE 2b

The reaction was carried out in the like manner as in Example 1a except that the reaction temperature was 60° C. The results are also shown in the following Table 1.

EXAMPLES 2c TO 2i

The reaction was carried out in the like manner as in Example 1a except that the reaction temperatures and the kinds of bases were changed. The results are also shown in the following Table 1.

TABLE 1

| Example No. | Base Name | Qty. (mole) | Temp. (° C.) | Time (h) | Conversion of β-Iso- phorone (%) | Selectivity of 4-Oxo- isophorone (%) | Selectivity of Aldehyde (%) | Recovery of Base (%) |
|---|---|---|---|---|---|---|---|---|
| 2a | Pyridine | 39 | 100 | 4 | 99.8 | 73.8 | 1.3 | 90.7 |
| 2b | Pyridine | 39 | 60 | 4 | 36.1 | 67.9 | 1.9 | 95.8 |
| 2c | TEA | 39 | 40 | 4 | 100.0 | 67.9 | 12.1 | 67.9 |
| 2d | TEA | 39 | 30 | 1 | 48.7 | 60.2 | 11.9 | 76.2 |
| 2e | TEA | 6.8 | 60 | 4 | 99.6 | 65.9 | 8.4 | 46.2 |
| 2f | TEA | 2 | 60 | 4 | 90.8 | 75.0 | 4.7 | 4.8 |
| 2g | TPA | 39 | 60 | 4 | 100.0 | 69.1 | 9.7 | 80.8 |
| 2h | TBA | 39 | 60 | 4 | 99.2 | 65.9 | 8.8 | 75.8 |
| 2i | BMA | 6.8 | 60 | 4 | 99.3 | 71.3 | 4.3 | 42.4 |

Notes
Qty.: The quantity per 100 moles of β-isophorone
TEA: Triethylamine
TPA: Tri-n-propylamine
TBA: Tri-n-butylamine
BMA: Benzyldimetylamine
Aldehyde: 5,5-dimethyl-3-oxo-1-cyclohexene carbaldehyde (Formula [II])

EXAMPLE 3Aa

Step (3A)

To a 100 ml three-necked flask were fed 1 g of strongly acidic ion exchange resin catalyst (trade name: Amberlyst 15E made by Japan Organo Ltd.), 10.2 g of 4-oxoisophorone and 15.0 g of acetic anhydride, and reaction was carried out at 50° C. for 7.5 hours under nitrogen atmosphere at an atmospheric pressure with stirring. The reaction mixture was then cooled and analyzed by gas chromatography to obtain the result that the degree of conversion of reactant was 93.9% and the selectivity for trimethylhydroquinones was 90.0%. By comparing the retention time in gas chromatography and the result in mass spectrometry with those of separately synthesized standard sample, the reaction product was identified as trimethylhydroquinone diacetate. The results are shown in the following Table 2A.

EXAMPLES 3Ab AND 3Ac

The reaction was carried out in the like manner as in Example 3Aa except that the reaction temperatures and the quantities of acetic anhydride were changed. The results are also shown in the following Table 2A.

EXAMPLE 3Ba

Step (3B)

A stainless steel tube of 1 m in length and 12 mm in inner diameter was filled will 15 ml of silica-alumina catalyst (trade name: N633L made by Nikki Chemical Corp.), the particle size of which was previously adjusted to 16 to 20 mesh. The reaction was carried out at 300° C. under atmospheric pressure with feeding 52.5 g of 4-oxoisophorone at a flow rate of 10.5 ml/h and acetic acid at a flow rate of 30 ml/h to the catalyst phase through respective preheating tubes. The contact time with the catalyst was 0.6 second. The reaction mixture was cooled and analyzed by gas chromatography to obtain results that the degree of conversion of reactant was 58% and the selectivity for trimethylhydroquinones was 75.4%. By comparing the retention time in gas chromatography and the result in mass spectrometry with those of separately synthesized standard sample, the reaction product was identified as trimethylhydroquinones. The results are shown in the following Table 2B.

EXAMPLES 3Bb AND 3Bc

The reaction was carried out in the like manner as in Example 3Ba except that the reaction temperatures were

TABLE 2A

| Example No. | Acid Catalyst Name | Qty. (wt. parts) | Qty. of Acetic Anhydride (mole) | Temp. (° C.) | Time (H) | Conversion of 4-oxo- isophorone (%) | Selectivity | | | |
|---|---|---|---|---|---|---|---|---|---|---|
| | | | | | | | TMHQ's (%) | TMHQ (%) | TMHQ-Ac (%) | TMHQ-2Ac (%) |
| 3Aa | Amberlyst | 10 | 220 | 50 | 8 | 93.9 | 90.0 | 0 | 0 | 90.0 |
| 3Ab | Amberlyst | 10 | 750 | 50 | 8 | 100 | 98.5 | 0 | 0 | 98.5 |
| 3Ac | Amberlyst | 10 | 300 | 100 | 8 | 98.4 | 89.5 | 0 | 0 | 89.5 |

Notes
Amberlyst: All Amberlysts were Amberlyst 15E
Qty. of Catalyst: Parts by weight per 100 parts by weight of 4-oxoisophorone
Qty. of Acetic Anhydride: Moles per 100 moles of 4-oxoisophorone
TMHQ: Trimethylhydroquinone
TMHQ's: Total of trimethylhydroquinones
TMHQ-Ac: Trimethylhydroquinone acetate
TMHQ-2Ac: Trimethylhydroquinone diacetate changed to 250° C. and 350° C., respectively. The results are also shown in the following Table 2B.

EXAMPLES 3Bd TO 3Bg

The reaction was carried out in the like manner as in Example 3Ba except that the catalysts were changed to HY-type zeolite (made by Catalyst & Chemical Industries Co., Ltd.), USY-type zeolite (made by Tosoh Corp.), H-mordenite (made by Tosoh Corp.) and ZSM-5 were used, respectively. The results are also shown in the following Table 2B.

TABLE 2B

| Example No. | Medium | Solid Acid | Temp. (° C.) | Conversion of 4-oxo-isophorone (%) | TMHQ's (%) | TMHQ (%) | TMHQ-Ac (%) | TMHQ-2Ac (%) | Recovery (%) |
|---|---|---|---|---|---|---|---|---|---|
| 3Ba | Acetic acid | Silica-alumina | 300 | 58.0 | 75.4 | 5.6 | 35.9 | 33.9 | 94 |
| 3Bb | Acetic acid | Silica-alumina | 250 | 17.7 | 69.7 | 0 | 26.7 | 43.0 | 93 |
| 3Bc | Acetic acid | Silica-alumina | 350 | 80.6 | 65.0 | 12.2 | 34.5 | 18.3 | 94 |
| 3Bd | Acetic acid | HY-type zeolite | 400 | 45.8 | 60.4 | 4.2 | 28.3 | 27.9 | 95 |
| 3Be | Acetic acid | USY-type zeolite | 500 | 50.2 | 58.8 | 3.7 | 29.5 | 25.6 | 94 |
| 3Bf | Acetic acid | H-mordenite | 450 | 26.5 | 35.1 | 18.6 | 14.0 | 2.5 | 95 |
| 3Bg | Acetic acid | ZSM-5 | 350 | 25.5 | 57.5 | 17.6 | 30.4 | 9.5 | 95 |

Notes
TMHQ: Trimethylhydroquinone
TMHQ's: Total of trimethylhydroquinones
TMHQ-Ac: Trimethylhydroquinone acetate
TMHQ-2Ac: Trimethylhydroquinone diacetate

EXAMPLE 4a

Step (4)

To a 500 ml flask was fed 10.0 g of reactant mixture containing 8.64% of trimethylhydroquinone diacetate, 6.24% of a mixture of 4-acetoxy-2,3,6-trimethylphenol and 4-acetoxy-2,3,5-trimethylphenol, and 75.7% of 4-oxoisophorone, and the flask was displaced with nitrogen. Then, 50.0 g of water, 1.0 g of 97% sulfuric acid and 11.3 g of acetic acid were added to the above reactants and they were stirred at 100° C. for 2 hours under atmospheric pressure. The reaction mixture was cooled to a room temperature and 30 ml of hexane was added. The deposited crystals were filtered off to obtain 0.941 g of trimethylhydroquinone at a yield of 90.0%. The purity of these crystals was 100% according to the gas chromatographic analysis. With the retention time in gas chromatography and the identification with a standard sample by the results of IR absorption and MS analysis, it was confirmed that the crystals were trimethylhydroquinone.

EXAMPLE 4b

A stainless steel tube of 1 m in length and 12 mm in inner diameter was filled will 15 ml of silica-alumina catalyst (trade name: N633L made by Nikki Chemical Corp.), the particle size of which was previously adjusted to 16 to 20 mesh. After displacing the reaction phase with nitrogen, reaction was carried out at 200° C. under atmospheric pressure with feeding 10.5 g of 33% solution of trimethylhydroquinone diacetate in toluene at a feed rate of 10.5 ml/h and 30 ml/h of water to the catalyst phase through respective preheating tubes. The contact time with the catalyst was 0.5 second. The reaction mixture was cooled and analyzed by gas chromatography to obtain results that the degree of conversion of reactant was 100% and the selectivity for trimethylhydroquinone was 95%.

In accordance with the method of the present invention as described above, it was made possible to produce inexpensively and in a high yield the trimethylhydroquinone which is useful as a raw material for preparing vitamin E, from inexpensive reactants through simplified process. In addition, it can be produced easily without causing the problem in waste treatment.

What is claimed is:

1. A method for producing trimethylhydroquinone comprising:

reacting isophorone in the presence of an acid catalyst and recovering β-isophorone by distillation;

oxidizing said β-isophorone in the presence of amorphous carbon and a base to obtain 4-oxoisophorone;

reacting said 4-oxoisophorone in a vapor phase with a carboxylic acid in the presence of a solid acid catalyst to obtain at least one compound represented by the following formula [I]:

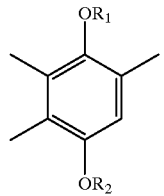

[I]

wherein $R_1$ and $R_2$ may be the same or different and are selected from hydrogen or an acyl group; and hydrolyzing compounds having at least one acyl group in the obtained reaction product represented by the formula [I], thereby obtaining trimethylhydroquinone.

2. A method for producing trimethylhydroquinone as claimed in claim 1, wherein said carboxylic acid reacting with 4-oxoisophorone is acetic acid.

3. A method for producing trimethylhydroquinone as claimed in claim 1, wherein said oxidation of β-isophorone is conducted in the presence of molecular oxygen as an oxidizing agent.

4. A method for producing trimethylhydroquinone as claimed in claim 1, wherein said base is an oxidation-resistant nitrogen-containing heterocyclic base.

5. A method for producing trimethylhydroquinone as claimed in claim 1 wherein the reaction product represented by the formula [I] is at least one compound selected from trimethylhydroquinone, 4-acetoxy-2,3,6-trimethylphenol, 4-acetoxy-2,3,5-trimethylphenol or trimethylhydroquinone diacetate.

6. A method for producing trimethylhydroquinone as claimed in claim 1 wherein the compound having at least one acyl group is selected from 4-acetoxy-2,3,6-trimethylphenol, 4-acetoxy-2,3,5-trimethylphenol or trimethylhydroquinone diacetate.

7. A method for producing trimethylhydroquinone comprising:

reacting 4-oxoisophorone in a vapor phase with a carboxylic acid in the presence of a solid acid catalyst to obtain at least one compound represented by the following formula [I]:

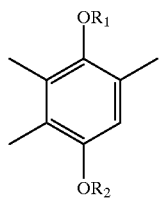

[I]

wherein $R_1$ and $R_2$ may be the same or different and are selected from hydrogen or an acyl group; and hydrolyzing compounds having at least one acyl group in the obtained reaction product represented by the formula [I], thereby obtaining trimethylhydroquinone.

8. A method for producing trimethylhydroquinone as claimed in claim 7, wherein said carboxylic acid reacting with 4-isophorone is acetic acid.

9. A method for producing trimethylhydroquinone as claimed in claim 7 wherein the reaction product represented by formula [I] is at least one compound selected from trimethylhydroquinone, 4-acetoxy-2,3,6-trimethylphenol, 4-acetoxy-2,3,5-trimethylphenol or trimethylhydroquinone diacetate.

10. A method for producing trimethylhydroquinone as claimed in claim 7 wherein the compound having at least one acyl group is selected from 4-acetoxy-2,3,6-trimethylphenol, 4-acetoxy-2,3,5-trimethylphenol or trimethylhydroquinone diacetate.

11. A method as claimed in claim 1 wherein the temperature of said vapor phase reaction ranges from about 200° C. to about 500° C.

12. A method as claimed in claim 7 wherein the temperature of said vapor phase reaction ranges from about 200° C. to about 500° C.

* * * * *